United States Patent [19]

Komatsubara et al.

[11] Patent Number: 5,374,554

[45] Date of Patent: Dec. 20, 1994

[54] MICROORGANISM AND PROCESS FOR PREPARING D-BIOTIN USING THE SAME

[75] Inventors: Saburo Komatsubara, Kawaguchi; Yuji Imai, Ashiya; Makoto Masuda, Takarazuka; Naoki Sakurai, Urawa, all of Japan

[73] Assignee: Tanabe Seiyaku Co., Ltd., Osaka, Japan

[21] Appl. No.: 4,111

[22] Filed: Jan. 13, 1993

[30] Foreign Application Priority Data

Jan. 24, 1992 [JP] Japan ................................. 4-051071

[51] Int. Cl.$^5$ .......................... C12N 15/00; C12N 1/21
[52] U.S. Cl. ................................ 435/252.3; 435/172.3; 435/119
[58] Field of Search ................... 435/119, 172.1, 172.3, 435/252.3; 935/38, 42

[56] References Cited

FOREIGN PATENT DOCUMENTS 62-155081  7/1987  Japan .
64-500081  1/1989  Japan .
 2-27980   1/1990  Japan .
 8701391   3/1987  WIPO .

OTHER PUBLICATIONS

Eisenberg et al. 1982, Antimicrobial Agents and Chemotherapy vol. 21(1):5–10.
Eisenberg, Max, 1987 "Biosynthesis of Biotin and Lipoic Acid" pp. 544–550, in F. C. Neidhart ed. *Escherichia coli* and *Salmonella typhimurium*; Cellular and Molecular Biology American Society for Microbiology, Washington, D.C.

*Primary Examiner*—Richard A. Schwartz
*Assistant Examiner*—Gary L. Brown
*Attorney, Agent, or Firm*—Birch, Stewart, Kolasch & Birch

[57] ABSTRACT

A microorganism derived from a host microorganism capable of producing d-biotin by introducing a recombinant plasmid being incorporated with a biotin gene cloned from a microorganism of the genus Serratia capable of producing d-biotin and further integrating an exogenous biotin gene into the chromosome, and a process for preparing d-biotin which comprises cultivating the microorganism in a culture medium so that d-biotin is formed and accumulated in the culture medium and collecting the d-biotin. The microorganism of the invention has an extremely high productivity of d-biotin, and hence, d-biotin can be produced in a large amount by cultivating the microorganism of the invention.

9 Claims, 4 Drawing Sheets

B:BamHI, Sm:SmaI

MICROORGANISM AND PROCESS FOR PREPARING D-BIOTIN USING THE SAME

The present invention relates to a novel microorganism and a process for preparing d-biotin using the same.

PRIOR ART d-Biotin is a vitamin indispensable to human beings or other animals and used as a raw material of drugs or as feed additives. As a process for preparing d-biotin by a fermentation method using a conventional fermentation medium, there is known a method using a genetically-engineered microorganism derived from the genus Escherichia or Serratia [cf. Japanese Patent Publication (Kohyo) No. 500081/1989, Japanese Patent First Publication (Kokai) No. 155081/1987 and Japanese Patent First Publication (Kokai) No. 27980/1990].

However, the production efficiency of d-biotin in these methods using the genetically-engineered microorganism is not so high, and hence, it has been required to construct a new microorganism having higher productivity of d-biotin and to develop an improved industrial fermentation method which can produce d-biotin with sufficiently high production efficiency using said microorganism.

As a result of various investigations, the present inventors have found that (i) a mutant microorganism obtained by mutating an actithiazic acid-resistant mutant so as to acquire a resistance against ethionine or S-aminoethylcysteine shows an increased productivity of d-biotin; (ii) a microorganism of the genus Serratia capable of producing d-biotin, wherein a fragment of chromosomal deoxyribonucleic acid (hereinafter referred to as "DNA") in charge of d-biotin production cloned from a microorganism of the genus Serratia is integrated into the chromosome by utilizing a transposon, shows an extremely increased productivity of d-biotin; (iii) when these microorganisms having higher productivity of d-biotin acquire an additional resistance against an acetic acid analogue such as chloroacetic acid, such microorganisms can show further extremely increased productivity of d-biotin; and further (iv) when the above microorganism (ii) or (iii) is incorporated with a recombinant plasmid comprising a vector and a biotin gene fragment cloned from an actithiazic acid-resistant mutant, the resultant microorganism shows a drastically increased productivity of d-biotin, and that d-biotin can advantageously be produced on an industrial scale by utilizing this microorganism (iv).

SUMMARY DESCRIPTION OF THE INVENTION

An object of the invention is to provide a microorganism derived from a host microorganism capable of producing d-biotin by introducing a recombinant plasmid being incorporated with a biotin gene cloned from a microorganism of the genus Serratia capable of producing d-biotin and further by integrating an exogenous biotin gene into the chromosome of said host microorganism.

Another object of the invention is to provide a process for preparing d-biotin which comprises cultivating said microorganism in a culture medium so that d-biotin is formed and accumulated in the culture medium and collecting the produced d-biotin.

Figure 1:
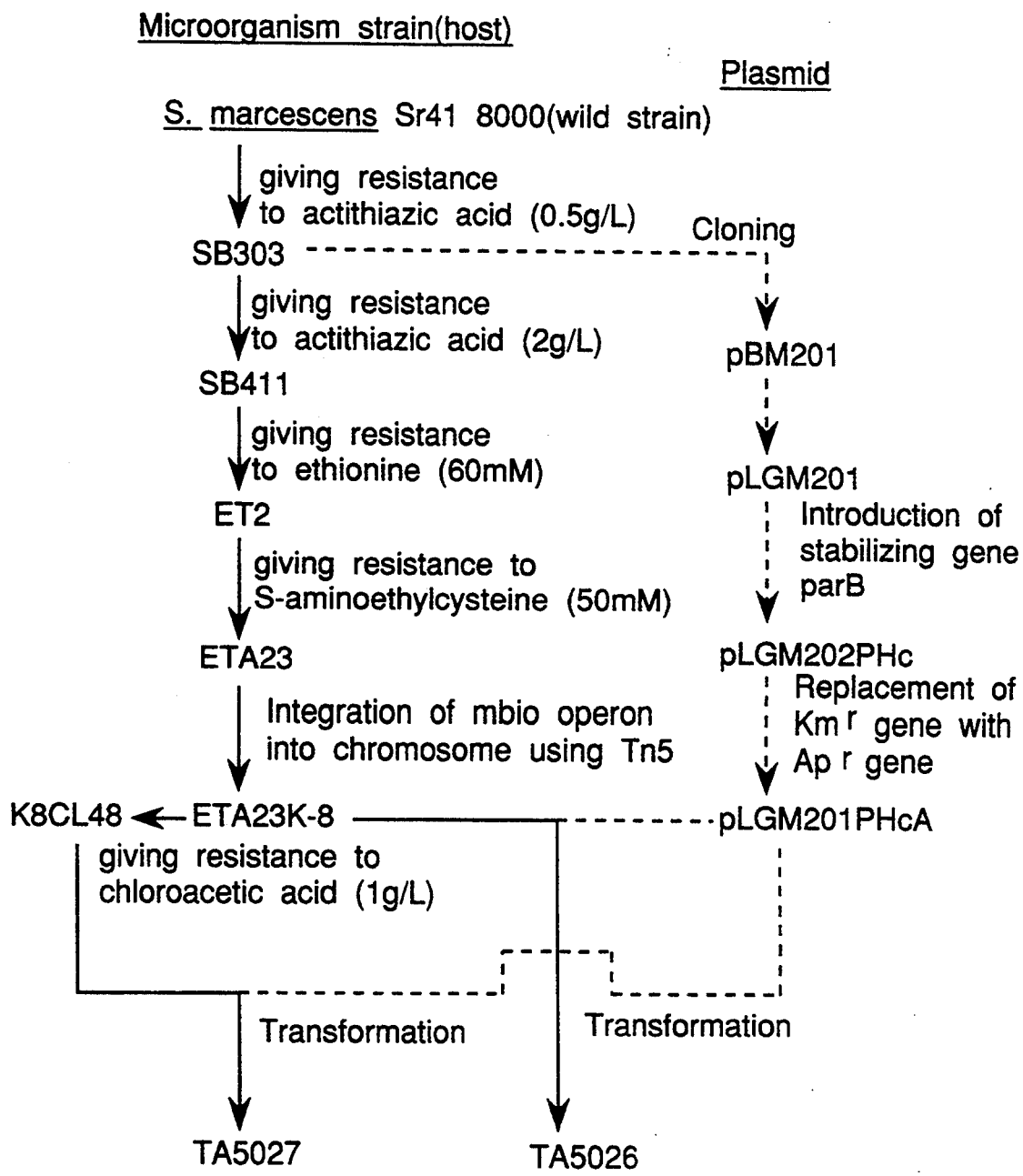
FIG. 1 illustrates the construction of novel microorganisms of the present invention, Serratia marcescens TA5026 and TA5027.

The following microorganisms:
1) *Serratia marcescens* TA5023 having the accession number FERM BP-4101;
2) *Serratia marcescens* TA5026 having the accession number FERM BP-4102; and
3) *Serratia marcescens* TA5027 having the accession number FERM BP-4103;

have been deposited under the terms and conditions of the Budapest Treaty with an International Depositing Authority. The depository is: Fermentation Research Institute Agency of Industrial Science and Technology, Osamu Suzuki, Dr., Director General; 1-3, Higashi 1-chome Tsukuba-shi, Ibaraki-ken 305, Japan.

DETAILED DESCRIPTION OF THE INVENTION

[A] Source of Biotin gene

A biotin gene referred to herein means any gene participating in the d-biotin production in vivo such as a gene encoding 7,8-diaminopelargonic acid aminotransferase (bioA), a gene encoding biotin synthetase (bioB), a gene encoding 7-keto-8-aminopelargonic acid synthetase (bioF), a gene encoding pimeloyl-CoA synthetase (bioC) and a gene encoding dethiobiotin synthetase (bioD), or a partial portion of these genes. A source of such genes includes microorganisms belonging to the genus Serratia [cf. Bergey's Manual of Systematic Bacteriology, Vol. 1, page 477 (1984)] which are capable of producing d-biotin. The biotin gene used in the present invention is preferably derived from a microorganism of the genus Serratia showing resistance against biotin analogues such as actithiazic acid, 5-(2-thienyl)valetic acid, dehydrobiotin, etc.

Such microorganisms include microorganisms showing actithiazic acid resistance, such as *Serratia marcescens* SB303 (FERM P-10119) and *Serratia marcescens* SB411 [cf. Japanese Patent First Publication (Kokai) No. 27980/1990]. In addition, microorganisms which do not show any resistance against biotin analogues such as a wild strain *Serratia marcescens* Sr41 8000 (FERM BP-487) can also be suitably used as a source of the biotin gene after making them acquire a resistance against biotin analogues by a known method as described in Japanese Patent First Publication (Kokai) No. 27980/1990.

There can also be used as a source of the biotin gene those microorganisms which, in addition to the resistance against biotin analogues, further show resistance against methionine analogues such as ethionine, resistance against lysine analogues such as S-aminoethylcysteine, and resistance against acetic acid analogues such as chloroacetic acid.

[B] Vector Plasmid

The vector plasmid used for constructing the recombinant plasmid together with the above biotin gene may be any plasmid which is replicable in transformed cells, but is preferably plasmids which have a copy number of 1 to several thousands and contain a resistance marker against an antibiotic such as ampicillin, kanamycin, chloramphenicol, etc., and further contain an appropriate promoter such as lac, tac, or trp. Moreover, the vector plasmids may further contain a plasmid stabilizing gene such as par and parB.

These vector plasmids include, for example, pLG339 [cf. Gene, Vol. 18, page 335 (1982)], pBR322 [cf. Gene, Vol. 2, page 95 (1977)], pUC18 [cf. Gene, Vol. 33, page 103 (1985)], pUC19 [cf. Gene, Vol. 33, page 103 (1985)], pHSG298 [cf. Gene, Vol. 61, page 63 (1987)], pHSG299 [cf. Gene, Vol. 61, page 63 (1987)], pKG1022 [cf. Biotechnology, Vol. 6, page 1402 (1988)], pKT240 [cf. Gene, Vol. 26, page 273 (1983)], and the like. Another suitable example of a vector plasmid is a plasmid pCHR81 which is a temperature-sensitive replicable plasmid derived from conjugative plasmid R388 wherein Tn5 is incorporated as a transposon and a kanamycin-resistant gene and a trimethoprim-resistant gene are contained as selection markers [cf. Gene, Vol. 56, page 283 (1987)].

The above-mentioned plasmids are commercially available, or may be prepared from microbial cells containing these plasmids by a conventional method, for example, by "cleared lysate method" (cf. Yasuyuki Takagi, "Procedure for Experiment in Genetic Engineering", page 125, published by Kodansha, 1980), or by "alkaline lysis method" [cf. Maniatis et al., "Molecular Cloning", page 368, Cold Spring Harbor Laboratory, U.S.A. (1982)].

[C] Host Microorganism

The host microorganism of the present invention may be any microorganism capable of producing d-biotin.

Particularly, preferable host microorganism is microorganisms of the genus Serratia having resistance against all of or any one of biotin analogues such as actithiazic acid, 5-(2-thienyl)valeric acid, dehydrobiotin, etc., acetic acid analogues such as chloroacetic acid, etc., methionine or methionine analogues such as ethionine, etc., and lysine analogues such as S-aminoethylcysteine, etc. Most preferable one is *Serratia marcescens* having resistances against actithiazic acid, ethionine and S-aminoethylcysteine or the *Serratia marcescens* which further has resistance against chloroacetic acid.

Such host microorganisms include, for example, *Serratia marcescens* having resistance against actithiazic acid and being capable of producing d-biotin, such as *Serratia marcescens* SB303 (FERM P-10119) and *Serratia marcescens* SB411 [Japanese Patent First Publication (Kokai) No. 27980/1990], *Serratia marcescens* TA5023 (FERM BP-4101) which contains a recombinant plasmid pLGM201 constructed by inserting a biotin gene into a vector pLG339, and the like. In addition, there can also suitably be used a wild strain *Serratia marcescens* Sr41 8000 (FERM BP-487) after making it acquire resistance against the above substances.

The above-mentioned resistances can be given to the host microorganisms by a known method. For example, an appropriate microorganism is subjected to a conventional mutagenic treatment and then cultivated on a minimum agar medium supplemented with the above substances against which said microorganism is to acquire the desired resistance, such as biotin analogues, acetic acid analogues, etc., for example, Davis-Mingioli minimum medium [Journal of Bacteriology, Vol. 60, page 17 (1950)] or a modified medium thereof wherein the carbon source is replaced with various sugars, organic acids or amino acids, at 27° to 37° C. for 3 to 7 days and the formed large colonies are isolated. Then, the isolated microorganisms are tested for their productivity of d-biotin in the fermentation culture medium by a microorganism quantification method utilizing *Lactobacillus plantarum* (cf. Seikagaku Jikken Koza, Vol. 13, page 355) to select a microorganism having the desired resistance.

The treatment for giving the resistance to the host microorganism may be done either after or before the introduction of a recombinant plasmid or integration of an exogenous biotin gene into the chromosome of the host microorganism.

[D] Preparation of Recombinant Plasmid

The biotin gene can be prepared from the above microorganisms containing the biotin gene by a conventional method, for example, by "cleared lysate method" [cf. Yasuyuki Takagi, "Procedure for Experiment in Genetic Engineering", page 125, published by Kodansha, 1980; Maniatis et al., "Molecular Cloning", page 86, Cold Spring Harbor Laboratory, U.S.A. (1982)]. For example, a chromosome containing the biotin gene is digested with an appropriate restriction enzyme and the obtained gene fragments are subjected to an agarose gel electrophoresis. Then, a fraction containing the biotin gene fragment is separated from the agarose gel and subjected to an electrophoretic elution method [cf. Maniatis et al., "Molecular Cloning", page 164, Cold Spring Harbor Laboratory (1982)] using a dialysis tube.

Thereafter, a vector plasmid is partially digested with an appropriate restriction enzyme (e.g. EcoRI, HindIII, BamHI, SalI, etc.) and the obtained partially digested fragment is ligated to the above biotin gene fragment by a DNA ligase (e.g. T4 ligase, *E. coli* DNA ligase, etc.) to prepare a recombinant plasmid. The vector plasmid may be a plasmid incorporated with a DNA fragment in charge of plasmid stabilizing gene such as parB [Journal of Molecular Biology, Vol. 203, page 119 (1988)] or a plasmid containing an appropriate selection marker gene. Then, a restriction enzyme-deficient d-biotin-requiring mutant [e.g. *Escherichia coli* χ1776 strain (ATCC31244); Molecular Cloning of Recombinant DNA, page 248, ed. by Scott and Werner, Academic Press (1977), etc.] is transformed with the above-obtained recombinant plasmid DNA and those microorganisms which are resistant against kanamycin and do not require d-biotin on a culture medium supplemented with 7-keto-8-aminopelargonic acid are isolated, followed by extraction of a plasmid DNA from the obtained clone to give the desired recombinant plasmid.

[E] Host Microorganism Wherein Biotin Gene is Incorporated into Chromosome

A host microorganism wherein a biotin gene is incorporated into the chromosome can be prepared by ligating an exogenous biotin gene to a plasmid which contains a transposon and a marker gene and introducing said plasmid into the host microorganism.

The plasmid includes pCHR81 plasmid which is constructed for integrating a transposon into a chromosome [Gene, Vol. 56, page 283 (1987)]. The plasmid pCHR81 contains an incorporated transposon Tn5 and has a kanamycin-resistant gene and trimethoprim-resistant gene as selection marker genes. The exogenous gene is ligated to an appropriate portion of Tn5 utilizing a restriction enzyme site such as SmaI, SalI, BamHI, etc. and the resulting recombinant plasmid is then introduced into the host microorganism.

Before introducing the recombinant plasmid into the host microorganism, the plasmid wherein the exogenous gene is ligated is preferably modified by a modification system of microorganisms of the genus Serratia. For example, such a modification can be conducted by introducing the plasmid wherein the exogenous gene is ligated into *Serratia marcescens* TT392 (a mutant strain of *Serratia marcescens* Sr41) [Journal of Bacteriology, Vol. 161, page 1 (1985)] by the method of Takagi and Kisumi [Journal of Bacteriology, Vol. 161, page 1 (1985)] and isolating the plasmid from the obtained transformed microorganism by the cleared lysate method.

The modified plasmid is then introduced into a host microorganism by the method of Takagi and Kisumi and the host microorganism is cultivated at about 37° C. for several hours and the obtained culture solution, after being appropriately diluted, is applied onto a nutrient agar plate. Then, cultivation is done at 30° C. overnight to form colonies and those colonies showing kanamycin resistance and trimethoprim sensitivity are selected. After the colonies are isolated, the chromosomal DNA from the microbial cells is subjected to Southern blotting analysis using a probe corresponding to an appropriate portion within Tn5 DNA and thereby the strain showing a DNA band at the site of predicted nucleotide number can be identified as the host microorganism of the genus Serratia wherein the exogenous biotin gene is integrated into the chromosome.

[F] Preparation of Microorganism of the Genus Serratia Containing a Recombinant Plasmid Which Contains a Cloned Biotin Gene Fragment The recombinant plasmid constructed by incorporating a biotin gene into a vector plasmid can be introduced into the host microorganism wherein a biotin gene is incorporated into the chromosome, for example, by the method of Takagi and Kisumi. The transformed microorganism can be selected by the drug-resistance marker of the recombinant plasmid. The recombinant microorganism thus obtained includes, for example, *Serratia marcescens* TA5027 (FERM BP-4103) which is prepared by introducing a recombinant plasmid pLGM201PHcA containing a d-biotin gene fragment into a host microorganism *Serratia marcescens* K8CL48 which has resistances against actithiazic acid, ethionine, S-aminoethylcysteine and chloroacetic acid and contains an exogenous d-biotin gene fragment in the chromosome; *Serratia marcescens* TA5026 (FERM BP-4102) which is prepared by introducing a recombinant plasmid pLGM201PHcA containing a d-biotin gene fragment into a host microorganism *Serratia marcescens* ETA23-K8 which has resistances against actithiazic acid, ethionine and S-amino-ethylcysteine and contains an exogenous d-biotin gene fragment in the chromosome; and the like.

[G] Cultivation

The thus prepared microorganism capable of producing d-biotin is cultivated so that d-biotin is formed and accumulated in the culture medium at a high concentration.

The medium used for the production of d-biotin includes any conventional medium wherein the microorganism can grow. Suitable medium contains a carbon source such as saccharides (e.g. glucose, sucrose, molasses, etc.), organic acids (e.g. fumaric acid, citric acid, etc.), or alcohols (e.g. glycerol, etc.); a nitrogen source such as inorganic ammonium salts (e.g. ammonium sulfate, ammonium chloride, etc.) or urea; and an organic nutrient such as corn steep liquor, peptone, yeast extract, or casein hydrolysate, and the like. The carbon source is usually contained in an amount of 10 to 30% by weight based on the whole weight of the medium, the nitrogen source is usually contained in an amount of 1 to 3% by weight based on the whole weight of the medium, and the organic nutrient is usually contained in an amount of 0 to 1% by weight based on the whole weight of the medium. The medium may further optionally contain a slight amount of potassium phosphate, magnesium sulfate, ferrous sulfate, sodium molybdate, etc. It may further optionally contain calcium carbonate, ammonium, etc. in order to adjust pH of the medium in a range of 6 to 8.

The microorganism of the present invention is inoculated into the above medium and cultivated by shaking culture at 25° to 37° C. or culture under aerobic conditions (e.g. aeration culture) for 3 to 7 days and thereby a significant amount of d-biotin can be formed and accumulated in the medium. The amount of d-biotin formed and accumulated in the medium can further be increased by adding the above medium components to the medium at a suitable time or continuously during cultivation.

[H] Isolation and Purification of D-biotin from Culture Solution

From the thus obtained d-biotin containing culture solution, d-biotin can be isolated and purified in the following manner.

First, the solution after fermentation is acidified with hydrochloric acid and then the microbial cells are removed with a microfilter of hollow fiber type. The resultant filtrate is passed through a column filled with a high porous type synthetic adsorbent to adsorb d-biotin in the filtrate to the adsorbent. After the column is washed with a diluted hydrochloric acid solution, the desired d-biotin is eluted by passing methanol—ammonia solution (1:9) and the like through the column.

Then, the eluate containing d-biotin is concentrated under reduced pressure and the concentrate is passed through a column filled with a strongly basic anion exchange resin to adsorb d-biotin to the resin. The column is washed with water and then d-biotin is eluted with an aqueous ammonia and the like. The eluate is again concentrated under reduced pressure and is adjusted to around pH 3.0 with hydrochloric acid and the like. The concentrate is cooled at 5° to 10° C. and allowed to stand overnight, thereby d-biotin is crystallized. The obtained crystals are then separated by filtration and dried to give d-biotin in crystalline form at a high yield.

EXAMPLES

The present invention is illustrated by the following Examples but should not be construed to be limited thereto.

In the Examples, d-biotin was measured by the microorganism quantification method utilizing *Lactobacillus plantarum* [cf. Seikagaku Jikken Koza, Vol. 13, page 355; ed. by Zenji Nose et al., published by Tokyo Kagaku Dojin (1975)].

Example 1

(1) Preparation of Host Microorganism Having Resistance Against Actithiazic Acid, Ethionine and S-aminoethylcysteine (A): Cells of *Serratia marcescens* SB411 which has resistance against actithiazic acid and is capable of producing d-biotin (Japanese Patent First Publication (Kokai) No. 27980/1990) are subjected to a mutagenesis treatment by the method of Edelberg et al. [Biochemical and Biophysical Research Communications, Vol. 18, page 788 (1965)] and cultivated in a nutrient culture medium (glucose 0.5%, peptone 1.0%, meat extract 0.3%, yeast extract 1.0%, sodium chloride 0.5%) for 1 hour. The culture solution is centrifuged (1,000×g) and the obtained cells are washed three times with physiological saline by centrifugation. The cells are suspended in physiological saline and applied onto a minimum agar plate (glucose 0.5%, potassium dihydrogen phosphate 0.3%, dipotassium hydrogen phosphate 0.7%, magnesium sulfate 7 hydrate 0.01%, agar 1.5%) containing 60 mM DL-ethionine at 1 to 10×10$^5$ cells per plate. After cultivation at 30° C. for 5 days, formed large colonies are isolated to give ethionine-resistant strains.

(B): Then, the obtained resistant strains are tested for their productivity of d-biotin in a fermentation medium (sucrose 10%, urea 1%, dipotassium hydrogen phosphate 0.1%, magnesium sulfate 7 hydrate 0.1%, ferrous sulfate 7 hydrate 0.01%, calcium carbonate 2%) by the method described in Japanese Patent First Publication No. 27980/1990 to give a strain Serratia marcescens ET2 which shows a significantly increased productivity of d-biotin as compared to the parent strain.

The amount of d-biotin produced by this strain was 24 mg/l while the amount of d-biotin produced by the parent strain was 16 mg/l.

(C): The obtained Serratia marcescens ET2 cells are subjected to mutagenesis treatment in the same manner as in the above process (A) and then applied onto a minimum agar plate containing 50 mM S-aminoethylcysteine at 1 to 10×10$^5$ cells/plate. After cultivation at 30° C. for 5 days, formed large colonies are isolated to give S-aminoethylcysteine-resistant strains. These strains are tested for their productivity of d-biotin in the fermentation medium as in the above process (B) to give a strain Serratia marcescens ETA23 which shows a significantly increased productivity of d-biotin as compared to the parent strain.

The amount of d-biotin produced by this strain was 33 mg/l while the amount of d-biotin produced by the parent strain was 23 mg/l.

Figure 3:
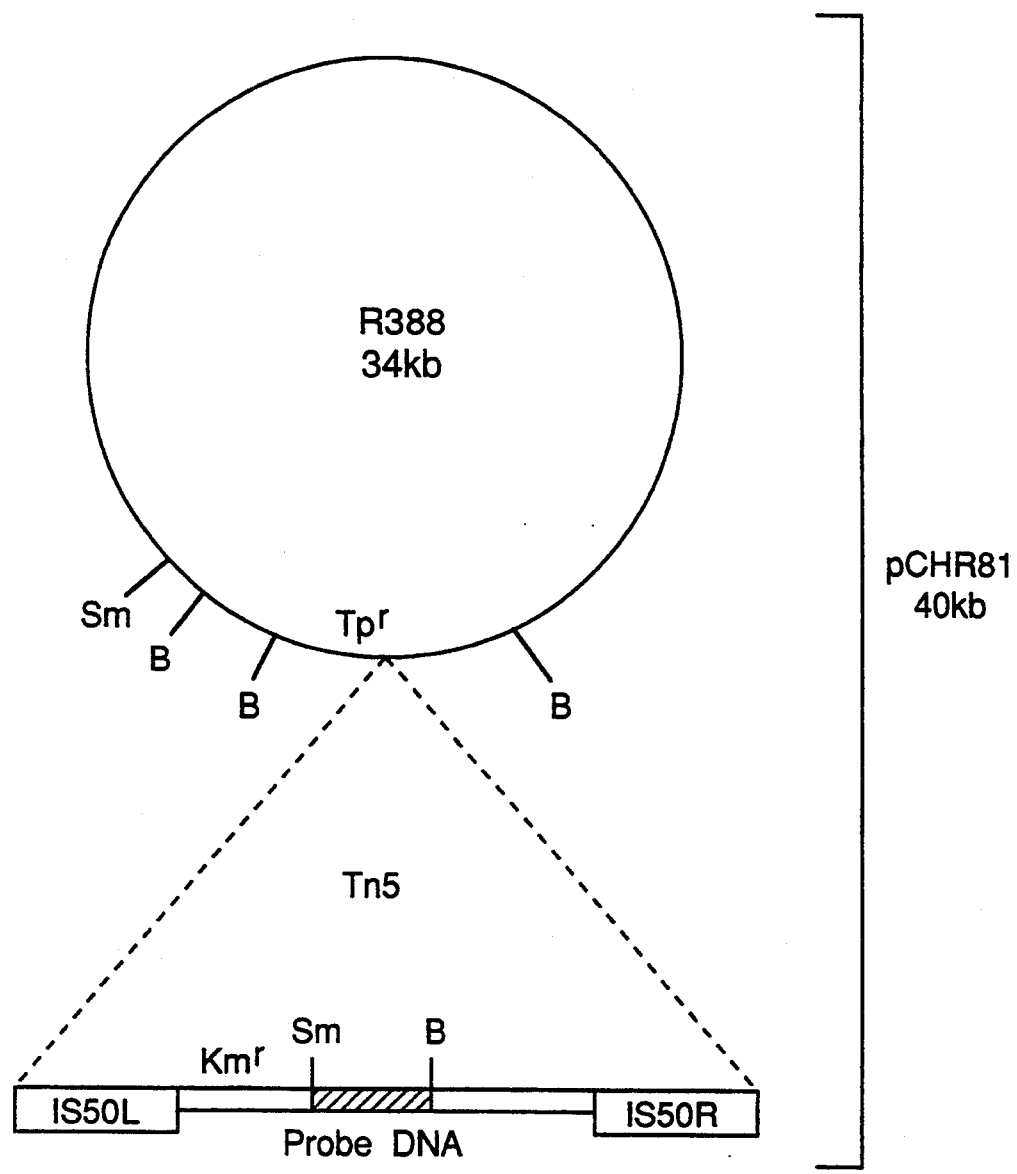
FIG. 3 shows the position of transposon Tn5 in a recombinant plasmid pCHR81.

(2) Integration of Exogenous Biotin Gene into Chromosome of Host Microorganism (A): Escherichia coli MC1061 containing pCHR81 [Gene, Vol. 56, page 283 (1987)] is inoculated into L-broth (800 ml) containing 0.2% glucose and subjected to shaking culture at 30° C. for 16 hours. The cells are collected by centrifugation and lysed with lysozyme and sodium lauryl sulfate. Then, sodium chloride is added to the lysate at a final concentration of 1M and the resultant lysate is subjected to centrifugation (100,000×g, 30 min). The supernatant is separated and is treated with phenol, supplemented with ethanol and subjected to centrifugation. The precipitate is dissolved in 10 mM Tris HCl—1 mM ethylenediamine tetraacetic acid 2 Na (pH 7.5) and the solution is subjected to density gradient centrifugation equilibrated with cesium chloride—ethidium bromide (200,000×g, 16 hours) to separate and purify a plasmid DNA to give pCHR81 DNA (0.3 mg)(FIG. 3).

(B): A recombinant plasmid pBM201, which is constructed by treating a chromosomal DNA isolated from Serratia marcescens SB303 and a vector plasmid pBR322 with HindIII and EcoRI and then ligating them together (cf. Japanese Patent First Publication No. 27980/1990; Example 2), is isolated in the same manner as in the process (2)(A). DNA (0.5 mg) of this plasmid is completely digested with restriction endonuclease BamHI and then subjected to agarose gel electrophoresis and the gel containing 6 kb DNA fragment is separated. This gel is put into a dialysis tube and an electroelution is conducted to give 6 kb DNA fragment (100 μg) which contains four genes (i.e. bioB, bioF, bioC, bioD genes) in charge of d-biotin production.

Figure 4:
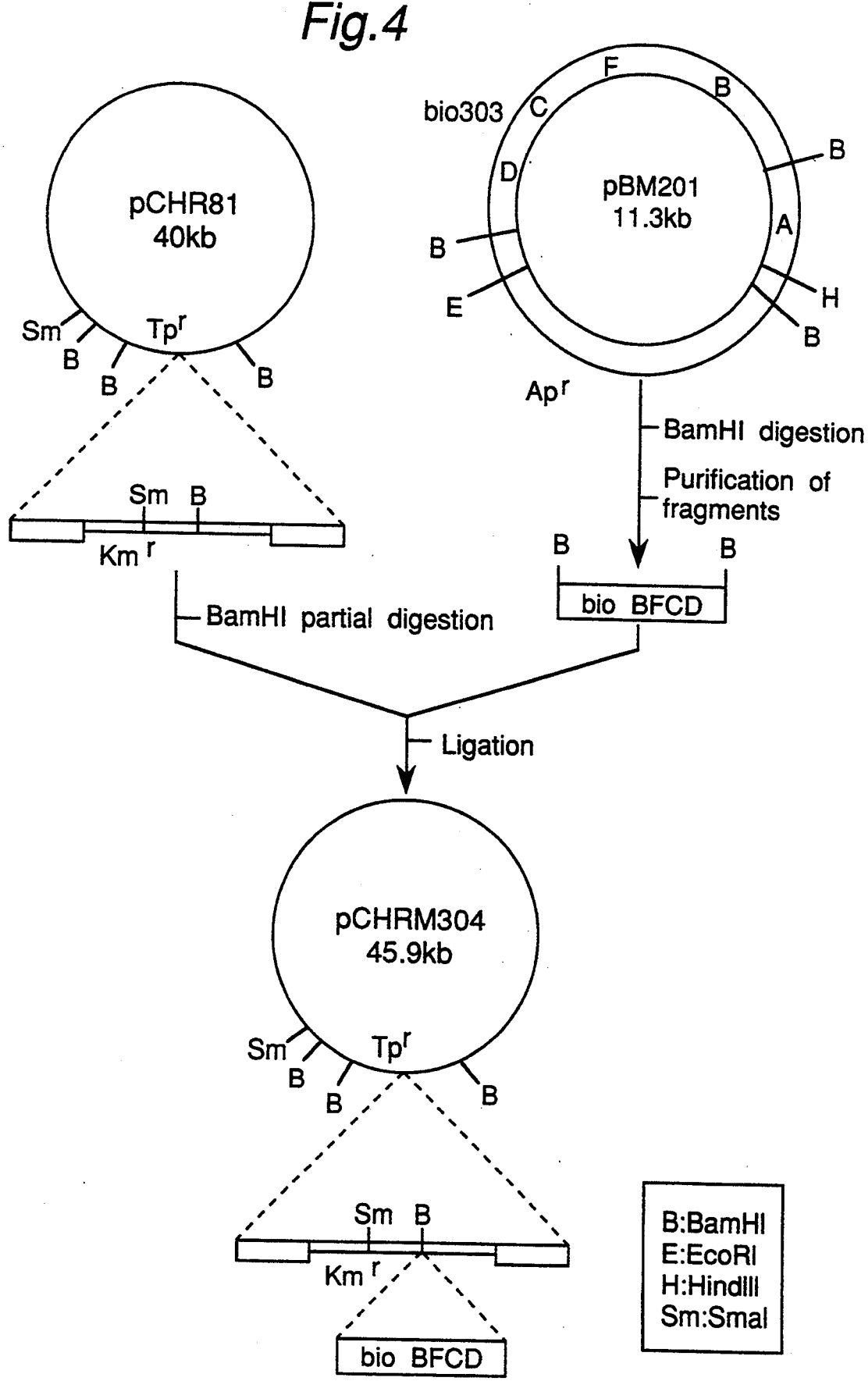
FIG. 4 illustrates the construction of a recombinant plasmid pCHRM304.

(C): pCHR81 DNA (1 μg) obtained in the process (2)(A) is partially digested with restriction enzyme BamHI. After heat-treatment for 10 minutes, the digested DNA is mixed with the biotin gene fragment (1 μg) of the process (B), and the mixture is treated with DNA ligase derived from T4 phage under usual conditions to ligate DNA chains to prepare a recombinant plasmid. Restriction enzyme-deficient d-biotin-requiring Escherichia coli χ1776 (ATCC31244) is transformed with the obtained recombinant plasmid DNA. The obtained transformed cells are applied onto a minimum agar plate (glucose 0.5%, ammonium sulfate 0.1%, dipotassium hydrogen phosphate 0.7%, potassium dihydrogen phosphate 0.3%, magnesium sulfate 7 hydrate 0.01%, diaminopimelic acid 0.01%, thymidine 0.004%, vitamin free casein hydrolysate 0.2%, agar 1.5%) containing kanamycin sulfate (100 μg/ml) and dl-dethiobiotin (0.2 μg/ml) and cultivated at 30° C. for 1 day. Formed colonies which are resistant against kanamycin and do not require d-biotin are isolated. Plasmid DNAs extracted from 10 colonies are digested with restriction enzyme BamHI and the obtained fragments are subjected to agarose gel electrophoresis analysis to give a recombinant plasmid pCHRM4304 wherein the 6 kb biotin gene fragment is inserted at the BamHI site within Tn5 of pCHR81 (FIG. 4). In this recombinant plasmid, the Tn5 fragment is ligated in the same direction as that in pCHR81.

(D): DNA of the recombinant plasmid pCHRM304 obtained in the process (C) is incorporated into cells of strain TT392, which is a restriction enzyme-deficient strain of Serratia marcescens, by the method of Takagi and Kisumi to give transformed cells. After cultivating the obtained transformed cells, a plasmid DNA is isolated and purified therefrom by the cleared lysate method to give DNA (250 μg) of the recombinant plasmid modified by the modification system of Serratia marcescens. Then, this recombinant plasmid DNA is incorporated into Serratia marcescens ETA23 capable of producing d-biotin by the method of Takagi and Kisumi and the cells are cultivated at 37° C. for 7 hours. After being diluted appropriately, the culture solution is applied to a nutrient agar plate supplemented with kanamycin sulfate (50 μg/ml) and is cultivated at 30° C. overnight to form colonies. The obtained 1500 colonies are examined for the presence of kanamycin resistance and trimethoprim resistance to select 8 colonies which are resistant against kanamycin and sensitive to trimethoprim.

These transformed strains are isolated and a chromosomal DNA is extracted from the cells and digested with each of restriction enzymes, HindIII and BamHI. The obtained DNA fragments are subjected to agarose gel electro-phoresis and then Southern blotting analysis is conducted using the BamHI—SmaI fragment (540 bp) of Tn5 present in pCHR81 as a probe to confirm that Tn5 containing the biotin gene fragments (bioB, bioF, bloC, bioD genes) is inserted into the chromosome in the transformed cells expressing kanamycin resistance and trimethoprim sensitivity. Then, these transformed cells are tested for their productivity of d-biotin in a fermentation medium (sucrose 10%, urea 1%, dipotassium hydrogen phosphate 0.1%, magnesium sulfate 7 hydrate 0.1%, ferrous sulfate 7 hydrate 0.01%, calcium carbonate 2%) by the method described in Japanese Patent First Publication No. 27980/1990, thereby a strain which shows the most increased productivity of d-biotin as compared to the parent strain, Serratia marcescens ETA23-K8, is obtained.

The above Southern blotting analysis further confirmed that, in case of the HindIII digestion, the transformed cells expressing kanamycin resistance and trimethoprim sensitivity showed a DNA band at the same site as that of the HindIII fragment of control pCHRM304, and on the other hand, the chromosome of the parent strain ETA23 did not show a DNA band reacting with the probe. The analysis further confirmed that, in case of the BamHI digestion, the transformed cells expressing kanamycin resistance and trimethoprim sensitivity showed a DNA band having a size different from that of the BamHI fragment of control pCHRM304, and on the other hand, the chromosome of the parent strain ETA23 did not show a DNA band reacting with the probe.

(3) Acquisition of Resistance Against Chloroacetic Acid by Host Microorganism Wherein an Exogenous Biotin Gene is Integrated into the Chromosome The Serratia marcescens ETA23-K8 cells obtained in the above process are subjected to mutagenesis treatment by the method of Ederberg et al. and cultivated in a nutrient medium for 1 hour. The culture solution is centrifuged and the obtained cells are washed three times with physiological saline by centrifugation. The cells are suspended in physiological saline and applied onto a minimum agar plate (L-proline 0.1%, ammonium sulfate 0.1%, potassium dihydrogen phosphate 0.3%, dipotassium hydrogen phosphate 0.7%, magnesium sulfate 7 hydrate 0.01%, agar 1.5%) supplemented with chloroacetic acid (1 mg/ml) at 1 to $10 \times 10^5$ cells per plate. After cultivation at 30° C. for 5 days, formed large colonies are isolated to give a chloroacetic acid-resistant strain, Serratia marcescens K8CL48.

The obtained drug-resistant strain was tested for its productivity of d-biotin in a fermentation medium (glucose 5%, urea 1%, potassium dihydrogen phosphate 0.1%, magnesium sulfate 7 hydrate 0.1%, ferrous sulfate 7 hydrate 0.01%, corn steep liquor 0.6%, calcium carbonate 2%), and as a result, this strain produced 26 mg/l of d-biotin during 48 hour cultivation while the parent strain produced 13 mg/l of d-biotin.

(4) Preparation of Recombinant Plasmid Containing Biotin Gene Fragment

Serratia marcescens TA5023 (FERM BP-4101) is treated in the same manner as in the process (2)(A) to give DNA of pLGM201 having a kanamycin-resistant gene as a selection marker wherein the biotin gene fragment (bioA, bioB, bioC, bioD genes) derived from Serratia marcescens SB303 is incorporated into the EcoRI—HindIII digestion sites of vector pLG339.

Separately, from Escherichia coli HB101 containing plasmid pKG1022 having a plasmid-stabilizing gene parB, DNA (0.3 mg) of pKG1022 is obtained in the same manner as in the process (2)(A) and digested with restriction endonucleases EcoRI and BamHI. The obtained DNA fragments are subjected to agarose gel electrophoresis and a DNA band of 580 bp is cut off from the gel and subjected to the electroelution method to give a DNA fragment containing parB region.

The vector pLG339 DNA (0.3 mg) is obtained from Escherichia coli C600rm- (ATCC33525) containing the vector pLG339 in the same manner as in the process (2)(A). The obtained DNA is digested with restriction enzyme HincII and the digested DNA is ligated with the above DNA fragment containing parB region, which is blunt-ended with the Klenow enzyme, using DNA ligase. Escherichia coli HB101 is transformed with the ligated DNA. A clone expressing kanamycin resistance and tetracycline sensitivity is selected and analyzed for its restriction enzyme map of the plasmid DNA, and thereby a recombinant plasmid pLG339P, wherein parB is inserted into the HincII site of pLG339, is obtained.

The recombinant plasmid pLGM201 DNA is completely digested with EcoRI and HindIII. On the other hand, pLG339P obtained above is completely digested with EcoRI and then partially digested with HindIII. Both digested DNAs of pLGM201 and of pLG339P are combined and used for transformation of Escherichia coli χ1776 (ATCC31244). From transformed cells, a clone which is resistant against kanamycin and does not require biotin is selected to give a plasmid pLGM201PHc containing the biotin gene fragment derived from Serratia marcescens SB303, the plasmid-stabilizing gene and the kanamycin-resistant gene wherein parB is inserted into the HincII site of pLGM201.

From Escherichia coli HB101 containing a plasmid pKT240 having an ampicillin-resistant gene, pKT240 DNA is obtained in the same manner as in the process (2)(A) and digested with BamHI and BstPI. The obtained DNA fragments are subjected to agarose gel electrophoresis and a DNA band of 3 kb is cut off from the gel and subjected to the electroelution method to give a DNA fragment containing the ampicillin-resistant gene region. This fragment is blunt-ended with the Klenow enzyme.

Figure 2:
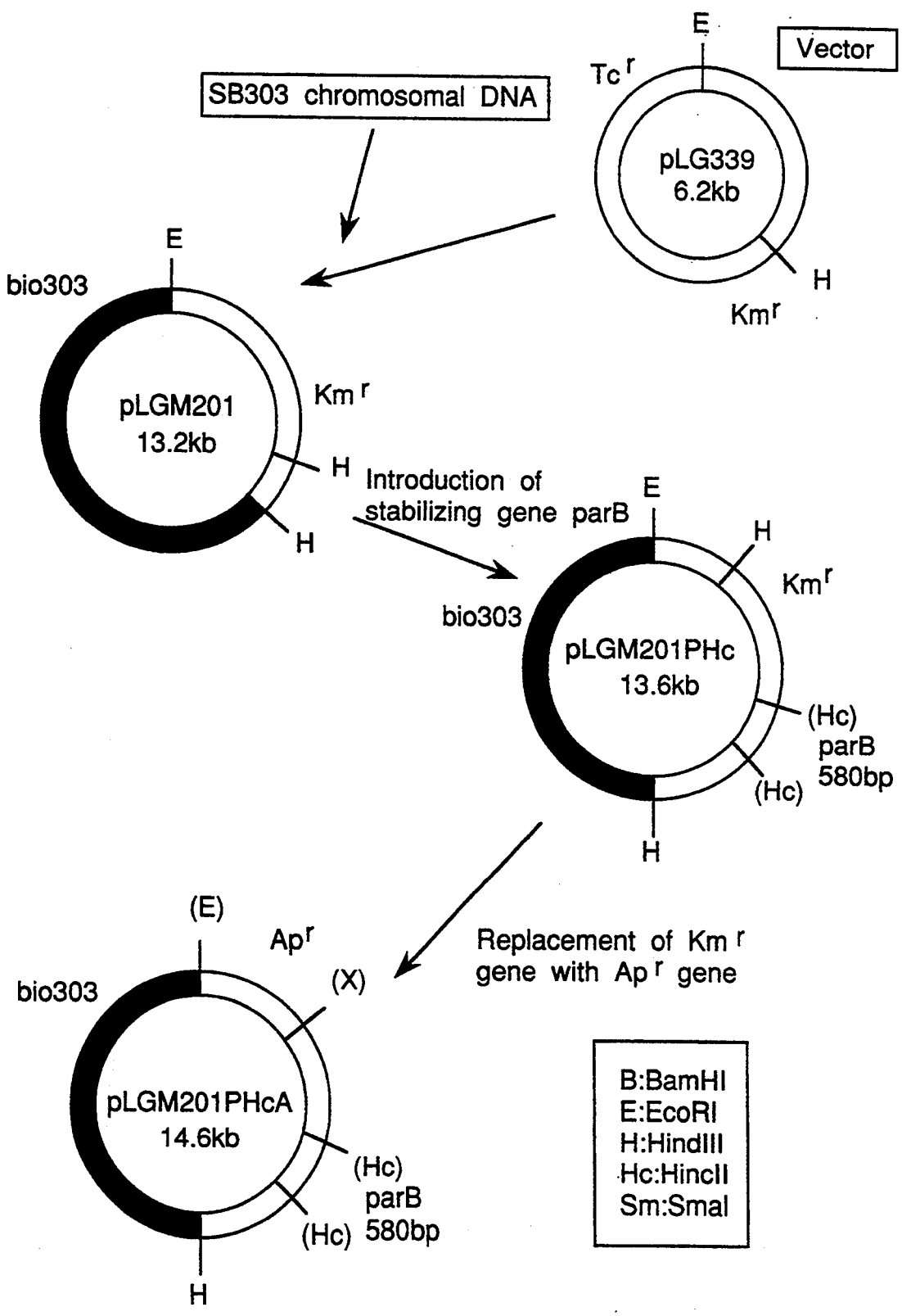
FIG. 2 illustrates the construction of a recombinant plasmid pLGM201PHcA.

On the other hand, the pLGM201PHc DNA obtained above is also digested with EcoRI and XhoI and blunt-ended with the Klenow enzyme. This DNA and the above blunt-ended DNA fragment containing ampicillin-resistant gene region are ligated with DNA ligase. Escherichia coli C600rm- is transformed with the ligated DNA to give a recombinant plasmid pLGM201PHcA wherein the kanamycin-resistant gene of pLGM201PHc is substituted with the ampicillin-resistant gene derived from pKT2401 (cf. FIG. 2).

(5) Preparation of the Desired Microorganism

The recombinant plasmid pLGM201PHcA obtained in the above process (4) is introduced into a restriction enzyme-deficient strain Serratia marcescens TT392 by the method of Takagi and Kisumi to give transformed cells. After cultivating the obtained transformed cells, a plasmid DNA is isolated and purified from the cells by the cleared lysate method to give a plasmid (300 μg) modified by the modification system of Serratia marcescens.

Then, this plasmid is introduced into Serratia marcescens ETA23K-8 cells obtained above by the method of Takagi and Kisumi and the cells are applied onto a nutrient agar plate supplemented with ampicillin (500 μg/ml) and cultivated at 30° C. overnight. Formed colonies are isolated from the medium to give Serratia marcescens TA5026 (FERM BP-4102) containing the recombinant plasmid pLGM201PHcA wherein the host microorganism is Serratia marcescens ETA23K-8 (cf. FIG. 1).

The plasmid DNA contained in this strain was confirmed to be identical to pLGM201PHcA DNA by the analysis of restriction enzyme digestion map.

Separately, the plasmid pLGM201PHcA is introduced into *Serratia marcescens* KSCL48 cells obtained above by the method of Takagi and Kisumi and the cells are applied onto a nutrient agar plate supplemented with ampicillin (500 μg/ml) and cultivated at 30° C. overnight. Formed colonies are isolated from the plate to give *Serratia marcescens* TA5027 (FERM BP-4103) containing pLGM201PHcA wherein the host microorganism is *Serratia marcescens* KSCL48 (cf. FIG. 1).

The plasmid DNA contained in this strain was confirmed to be identical to pLGM201PHcA DNA by the analysis of restriction enzyme digestion map.

Example 2

*Serratia marcescens* TA5026 obtained in Example 1 is cultivated on an agar slant of L-broth containing ampicillin (500 μg/ml) overnight and then a loopful of the cultivated cells is inoculated into a fermentation medium comprising a sterilized solution (15 ml) containing sucrose 15%, urea 1.5%, dipotassium hydrogen phosphate 0.1%, magnesium sulfate 7 hydrate 0.2%, ferrous sulfate 7 hydrate 0.01%, corn steep liquor 0.1% and calcium carbonate 1% (wherein sucrose is added to the solution after sterilization) in a 500 ml shaking flask. Then, a reciprocal shaking cultivation (7 cm stroke; 120 r.p.m.) is conducted at 30° C. for 120 hours.

The amount of d-biotin produced in the above culture was measured. The results are shown in Table 1 wherein control strains are *Serratia marcescens* SB411 (Japanese Patent First Publication (Kokai) No. 27980/1990) and *Serratia marcescens* TA5024 (Japanese Patent First Publication (Kokai) No. 27980/1990), which was obtained by introducing the recombinant plasmid pLGM201 into SB411.

TABLE 1

| | Name of microorganism (*Serratia marcescens*) | Amount of d-biotin produced and accumulated (mg/l) |
|---|---|---|
| Control | SB411 | 30 |
| | TA5024 | 150 |
| The present invention | TA5026 | 250 |

Example 3

Each of *Serratia marcescens* TA5026 and *Serratia marcescens* TA5027 is cultivated in an agar slant of L-broth containing ampicillin (500 μg/ml) or kanamycin sulfate (100 μg/ml) or in the same agar slant of L-broth containing neither ampicillin nor kanamycin sulfate overnight and then a loopful of the cultivated cells is inoculated into a fermentation medium comprising a sterilized solution (15 ml) containing glucose 7%, urea 1%, dipotassium hydrogen phosphate 0.1%, magnesium sulfate 7 hydrate 0.1%, ferrous sulfate 7 hydrate 0.01%, corn steep liquor 0.1% and calcium carbonate 4% (wherein glucose is added to the solution after sterilization) in a 500 ml shaking flask. Then, a reciprocal shaking cultivation (7 cm stroke; 120 r.p.m.) is conducted at 30° C. for 120 hours.

The amount of d-biotin produced in the above culture was measured. The results are shown in Table 2 wherein control strains are *Serratia marcescens* SB411 and *Serratia marcescens* TA5024.

TABLE 2

| | Name of microorganism (*Serratia marcescens*) | Amount of d-biotin produced and accumulated (mg/l) |
|---|---|---|
| Control | SB411 | 10 |
| | TA5024 | 54 |
| The present invention | TA5026 | 70 |
| | TA5027 | 96 |

Example 4

*Serratia marcescens* TA5026 obtained in Example 1 is cultivated in an agar slant of L-broth containing ampicillin (500 μg/ml) overnight and then a loopful of the cultivated cells is inoculated into a preculture medium comprising a sterilized solution (30 ml) containing sucrose 10%, urea 1%, dipotassium hydrogen phosphate 0.1%, magnesium sulfate 7 hydrate 0.2%, ferrous sulfate 7 hydrate 0.01%, corn steep liquor 0.6% and calcium carbonate 1% (wherein sucrose is added to the solution after sterilization) in a 500 ml shaking flask. Then, a reciprocal shaking cultivation (7 cm stroke; 120 r.p.m.) is conducted at 30° C. for 24 hours. The obtained preculture solution (14 ml) is inoculated into a fermentation medium [sucrose 15%, urea 1.5%, dipotassium hydrogen phosphate 0.08%, magnesium sulfate 7 hydrate 0.2%, ferrous sulfate 7 hydrate 0.01%, corn steep liquor 0.1%, calcium carbonate 4.2% and Disfoam CA220 (antifoaming agent, manufactured by Nippon Yushi K.K., Japan) 0.28%; 1.0 liter] and cultivated in a 1.8 liter jar fermenter at 30° C. at aeration rate of 0.5 liter/min. while the rate of agitating is regulated so that the dissolved oxygen concentration is maintained to 10% of the saturated concentration. From 48 to 120 hours after starting cultivation, an additional medium prepared separately (sucrose 67.5%, urea 5%, dipotassium hydrogen phosphate 0.15% and corn steep liquor 0.1%) is continuously added to the medium at the flow rate of 5.6 ml/h. And separately, from 48 to 120 hours after starting cultivation, 0.67 ml of 20% magnesium sulfate 7 hydrate and 0.97 ml of 2% ferrous sulfate 7 hydrate are added to the medium every 24 hours. The cultivation is conducted for 144 hours to give a culture solution (about 1.3 liters) containing 540 mg/l of d-biotin.

Example 5

*Serratia marcescens* TA5027 obtained in Example 1 is cultivated in an agar slant of L-broth containing ampicillin (500 μg/ml) overnight and then a loopful of the cultivated cells is inoculated into a preculture medium comprising a sterilized solution (30 ml) containing glucose 5%, urea 1%, dipotassium hydrogen phosphate 0.1%, magnesium sulfate 7 hydrate 0.2%, ferric sulfate 0.01%, corn steep liquor 0.6% and calcium carbonate 1% (wherein glucose is added to the solution after sterilization) in a 500 ml shaking flask. Then, a reciprocal shaking cultivation (7 cm stroke; 120 r.p.m.) is conducted at 30° C. for 24 hours. The obtained preculture solution (14 ml) is inoculated into a fermentation medium [glucose 5%, ammonium sulfate 0.5%, dipotassium hydrogen phosphate 0.2%, magnesium sulfate 7 hydrate 0.2%, ferric sulfate 0.001%, corn steep liquor 0.7% and Disfoam CA220 (antifoaming agent, manufactured by Nippon Yushi K.K., Japan) 0.28% (pH 7.0); 1.0 liter] and cultivated in a 1.8 liter jar fermenter at 30° C. at aeration rate of 0.5 liter/min. while the rate of agitating is regulated so that the dissolved oxygen concentration is maintained to 10% of the saturated concentration. The culture solution is regulated to pH 7.4 or more with a mixture of potassium hydroxide—ammonia. From 1 to 3 days after starting cultivation, an additional medium prepared separately (glucose 57.5%, ammonium sulfate 0.5%, dipotassium hydrogen phosphate 0.34%, magnesium sulfate 7 hydrate 0.2%, ferric sulfate 0.01% and corn steep liquor 2.75%) is continuously added to the medium at the flow rate of 3 ml/h to 15 ml/h. The cultivation is conducted for 3 days to give a culture solution (about 1.3 liters) containing 260 mg/l of d-biotin.

Example 6

The culture solution (6.0 liters) obtained in accordance with the procedures in Example 4 is acidified to pH 2.7 with hydrochloric acid and then the cells are removed with a microfilter (Microza SP113, manufactured by Asahi Chemical Industry Co., Ltd., Japan) to give a filtrate (7.6 liters). The obtained filtrate is passed through a column filled with a high porous type synthetic adsorbent (SP207, manufactured by Mitsubishi Kasei Corporation, Japan)(amount of the resin, 1000 ml; column diameter, 40 mm) at the flow rate of SV=2 to adsorb d-biotin in the filtrate to the adsorbent and then one liter of diluted hydrochloric acid (pH 3.0) is passed through the column at the flow rate of SV=2 to wash the adsorbent. Then, d-biotin is eluted by passing a methanol—ammonia solution (1:9) through the column at the flow rate of SV=2.

The eluate (1.8 liters) obtained above is concentrated under reduced pressure with a rotary evaporator to give a concentrate (900 ml). The obtained concentrate is then passed through a column filled with a strongly basic anion exchange resin (Diaion SA-11A, manufactured by Mitsubishi Kasei Corporation, Japan)(amount of the resin 100 ml; column diameter 20 mm) at the flow rate of SV=2 to adsorb d-biotin to the resin. The column is washed with water (200 ml) and d-biotin is eluted by passing 900 ml of 0.2N ammonium chloride—0.2N ammonia (1:1) through the column at the flow rate of SV=2. The obtained eluate (900 ml) is concentrated under reduced pressure to a volume of 60 ml and the concentrate is adjusted to pH 2.7 with conc. hydrochloric acid and allowed to stand at 10° C. or below overnight, thereby d-biotin is crystallized. The formed crystals are separated by filtration and dried to give crude crystals (4.5 g), which are recrystallized from the water solution to give 2.3 g of pure d-biotin.

EFFECTS OF THE INVENTION

The microorganism of the present invention, i.e. a microorganism derived from a host microorganism capable of producing d-biotin by introducing a recombinant plasmid being incorporated with a biotin gene cloned from a microorganism of the genus Serratia capable of producing d-biotin and further by integrating an exogenous biotin gene into the chromosome of said host microorganism, has an extremely high productivity of d-biotin, and hence, d-biotin can be produced in a large amount by cultivating the microorganism of the invention.

What is claimed is:

1. A host microorganism of the genus Serratia which can produce d-biotin, wherein:
   i) said host microorganism has resistance to a biotin analogue, a methionine analogue, and a lysine analogue,
   ii) an exogenous biotin gene is integrated into the chromosome of said host microorganism, and
   iii) said host microorganism is transformed with a recombinant plasmid which harbors an exogenous biotin gene cloned from a microorganism of the genus Serratia which can produce d-biotin.

2. The microorganism of claim 1 wherein said biotin gene is cloned from a microorganism of the genus Serratia having a resistance against a biotin analogue.

3. The microorganism of claim 1, wherein said recombinant plasmid is that being constructed by incorporating the biotin gene into vector plasmid pLG339.

4. The microorganism of claim 1 wherein said biotin analogue is a member selected from the group consisting of actithiazic acid, 5-(2-thienyl)valeric acid and dehydrobiotin, said methionine analogue is ethionine and said lysine analogue is S-aminoethylcysteine.

5. The microorganism of claim 3, wherein said biotin analogue is actithiazic acid, said methionine analogue is ethionine and said lysine analogue is S-aminoethylcysteine.

6. The microorganism of claim 1, wherein said host microorganism is a microorganism having a resistance against an acetic acid analogue.

7. The microorganism of claim 6 wherein said biotin analogue is a member selected from the group consisting of actithiazic acid, 5-(2-thienyl)valeric acid and dehydrobiotin, said methionine analogue is ethionine, said lysine analogue is S-aminoethylcysteine and said acetic acid analogue is chloroacetic acid.

8. *Serratia marcescens* TA5026 (FERM BP-4102).

9. *Serratia marcescens* TA5027 (FERM BP-4103).

* * * * *